United States Patent
Eckels et al.

(10) Patent No.: US 7,339,169 B1
(45) Date of Patent: Mar. 4, 2008

(54) SAMPLE ROTATING TURNTABLE KIT FOR INFRARED SPECTROMETERS

(75) Inventors: Joel Del Eckels, Livermore, CA (US); Gregory L. Klunder, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 11/606,616

(22) Filed: Nov. 29, 2006

(51) Int. Cl.
*G01N 21/01* (2006.01)

(52) U.S. Cl. .......................... 250/339.07; 250/339.09; 356/244; 356/246; 356/300

(58) Field of Classification Search .......... 250/339.07, 250/339.08, 339.09; 356/300, 301, 244, 356/246
See application file for complete search history.

(56) References Cited

U.S. PATENT DOCUMENTS

| | | | |
|---|---|---|---|
| 3,904,880 A | 9/1975 | Benz et al. | |
| 4,264,205 A | 4/1981 | Landa | |
| 4,785,170 A | 11/1988 | Witt | |
| 5,017,787 A | 5/1991 | Sato et al. | |
| 5,160,826 A | 11/1992 | Cohen et al. | |
| 5,206,510 A | 4/1993 | Wolf et al. | |
| 5,406,090 A | 4/1995 | Mattson et al. | |
| 5,679,954 A * | 10/1997 | Soloman | 250/339.08 |
| 6,373,567 B1 | 4/2002 | Wise et al. | |
| 6,611,334 B1 | 8/2003 | Fernando et al. | |
| 6,819,420 B2 * | 11/2004 | Kuebler et al. | 356/337 |
| 2006/0011829 A1 | 1/2006 | Scheidemann et al. | |

OTHER PUBLICATIONS

Kubik, J.J., "Rotation of Micro Samples for Infrared Spectrophotometer Analysis," Western Electric Technical Digest No. 3, Jul. 1966, 2 pages.

* cited by examiner

*Primary Examiner*—Dave Porta
*Assistant Examiner*—Casey Bryant
(74) *Attorney, Agent, or Firm*—Eddie E. Scott; John H. Lee

(57) ABSTRACT

An infrared spectrometer sample rotating turntable kit has a rotatable sample cup containing the sample. The infrared spectrometer has an infrared spectrometer probe for analyzing the sample and the rotatable sample cup is adapted to receive the infrared spectrometer probe. A reflectance standard is located in the rotatable sample cup. A sleeve is positioned proximate the sample cup and adapted to receive the probe. A rotator rotates the rotatable sample cup. A battery is connected to the rotator.

13 Claims, 3 Drawing Sheets

SAMPLE ROTATING TURNTABLE KIT FOR INFRARED SPECTROMETERS

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to infrared spectrometers and more particularly to a sample rotating turntable kit for infrared spectrometers.

2. State of Technology

U.S. Pat. No. 5,160,826 issued Nov. 3, 1992 to Joel A. Cohen et al for FT-IR spectrometer window and method, provides the following state of technology information: "FT-IR spectrometers are well known in the prior art. Such spectrometers may be used to identify compounds contained in a sample through recognition of the compounds, characteristic absorption of infrared radiation at various frequencies."

U.S. Pat. No. 5,206,510 issued Apr. 27, 1993 to Udo Wolf et al for spectroscopic analysis process for plastic mixtures, provides the following state of technology information: "The (U.S. Pat. No. 5,206,510) invention relates to method for the analysis of a plastic foil or film sample by determination of infrared transmission spectra in a Fourier transform spectrometer wherein the method comprises obtaining a plurality of distinct spectra while the specimen is rotated at an angular velocity so that the period of rotation is greater than the measuring time required to determine a single transmission spectrum and calculating the percentage contents of individual constituents in the specimen by averaging the data in the plurality of spectra."

The article, "Rotation of Micro Samples for Infrared Spectophotometer Analysis," in *Western Electric Technical Digest*, No. 3, July 1966, provides the following state of technology information: "When utilizing infrared spectrophotometers for analysis of materials to determine the chemical constituents thereof, a sample of material is normally placed in a sample holder so as to completely cover the portion of the sample holder through which the infrared beam is passed. However, in many instances only micro samples are available for the analysis and these samples, which do not fully cover the beam exposed portion of the sample holder are often impossible to center in the holder. As a result, the output response of the spectrophotometer may be substantially reduced. The method of this disclosure has been specifically developed for increasing the output of, and thereby the response of, the graphical recording device of an infrared spectrophotometer when a micro sample is utilized in the analysis. The increase in response is obtained by rotation of the sample holder carrying the micro sample during the period of time that the infrared beam is passing therethrough."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Spectroscopic methods based on reflectance measurements are becoming more popular for detection and identification of materials. In the near infrared wavelength range, typically defined as 700-2500 nanometers, diffuse reflectance measurements can be achieved using fiber optic bundles to deliver and collect the light. Light exiting the fiber reflects off of the sample and is partially absorbed at unique wavelengths based on the material. The reflected light is collected with the fiber and dispersed onto a detector which measures the intensity of the reflected light compared to a reflectance standard.

Sample surfaces of solids and powders can provide varying reflectance characteristics based on the particle size and/or angle of incidence of the light. In order to minimize these effects, samples can be rotated or translated linearly in front of the illuminating and collection optics. Although there are commercial products that accomplish this task, they are laboratory based and require large amounts of sample. The need for field analysis requires a sample rotator that can handle small amounts of samples and is battery powered. In addition, ambient lighting can interfere with the analysis, so it is necessary to eliminate, or minimize, the amount of stray light that can interact with the sample. It is also important to rotate out of synchronization with the data collection so that the sample is in a new position with each scan.

The present invention provides a portable infrared spectrometer sample rotating turntable apparatus. The apparatus has a rotatable sample cup containing the sample. The geometry is designed for measuring reflectance spectra with an infrared spectrometer. Reflectance measurements are common and have been tested in the near-infrared spectral range (700-2500 nm); however, the present invention is not limited to this range. A probe (e.g., fiber optic bundle), brings light to the sample in the rotating sample cup and returns the light to the infrared spectrometer for spectral analysis. A reflectance standard is located in the rotatable sample cup. A sleeve is positioned proximate the sample cup and adapted to receive the probe. The sleeve eliminates background light and keeps the probe aligned over the center of the sample cup. A rotator rotates the rotatable sample cup. A battery is connected to the rotator.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
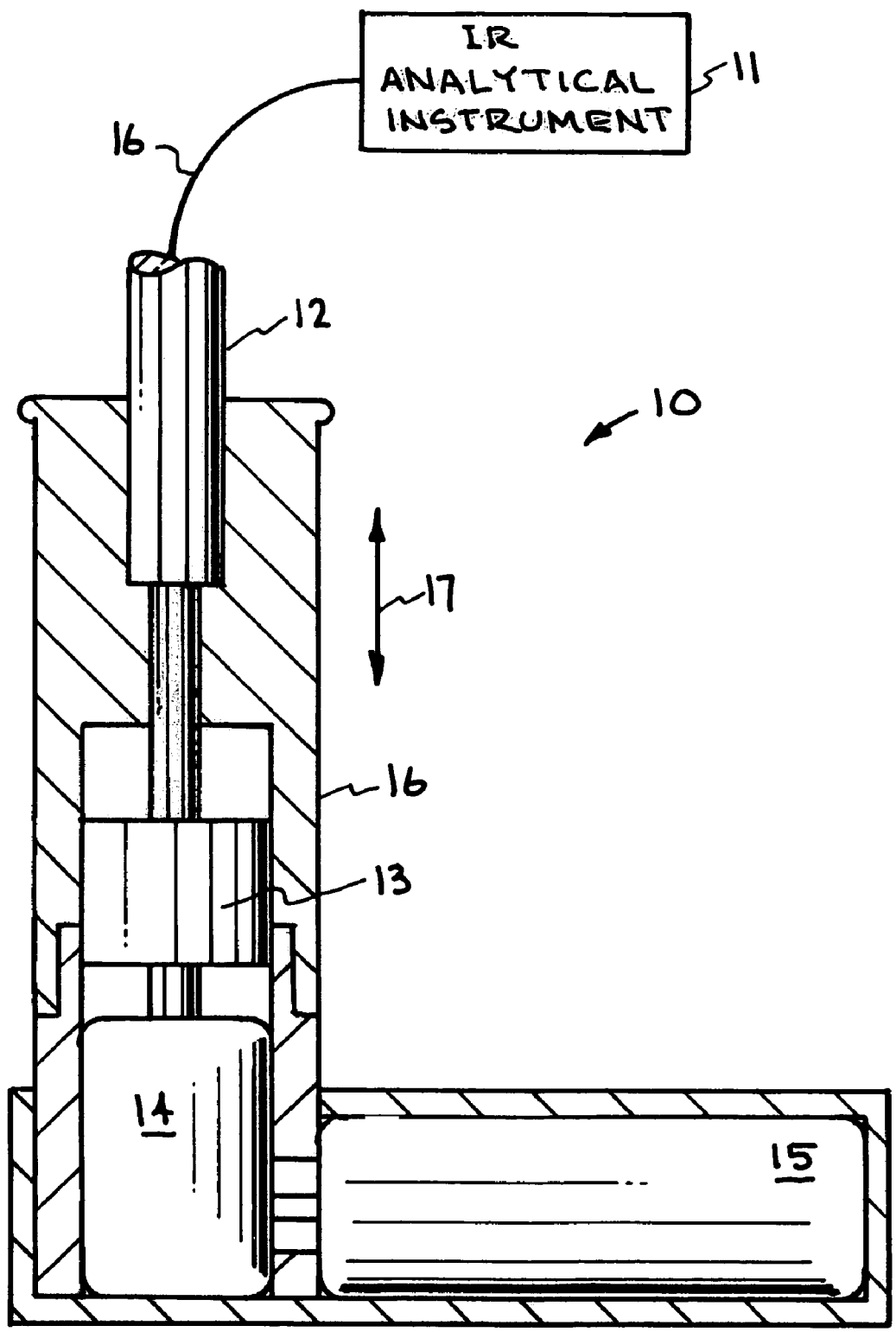
FIG. 1 illustrates an embodiment of a sample rotating turntable kit for an infrared spectrometer constructed in accordance with the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, an embodiment of a sample rotating turntable kit for an infrared spectrometer constructed in accordance with the present invention is illustrated. The kit is designated generally by the reference numeral 10. The kit 10 is used with an infrared spectrometer 11. The infrared spectrometer 11 has a probe 12 that delivers and collects light to and from a sample cup 13. The probe 12 uses a fiber optic bundle to deliver and collect light.

The kit 10 includes a rotatable sample cup 13 containing a sample. The sample cup 13 is adapted to receive the probe 12. A reflectance standard is located in the sample cup 13. A rotator 14 rotates the sample cup 13. A battery 15 is connected to the rotator and provides power to the rotator 14 for rotating the sample cup 13.

Light exiting a fiber optic in the probe 12 reflects off of the sample and is partially absorbed at unique wavelengths based on the sample material. The reflected light is collected with a fiber optic in the probe 12 and dispersed onto a detector in the spectrometer 11 which measures the intensity of the reflected light compared to a reflectance standard.

Figure 2:
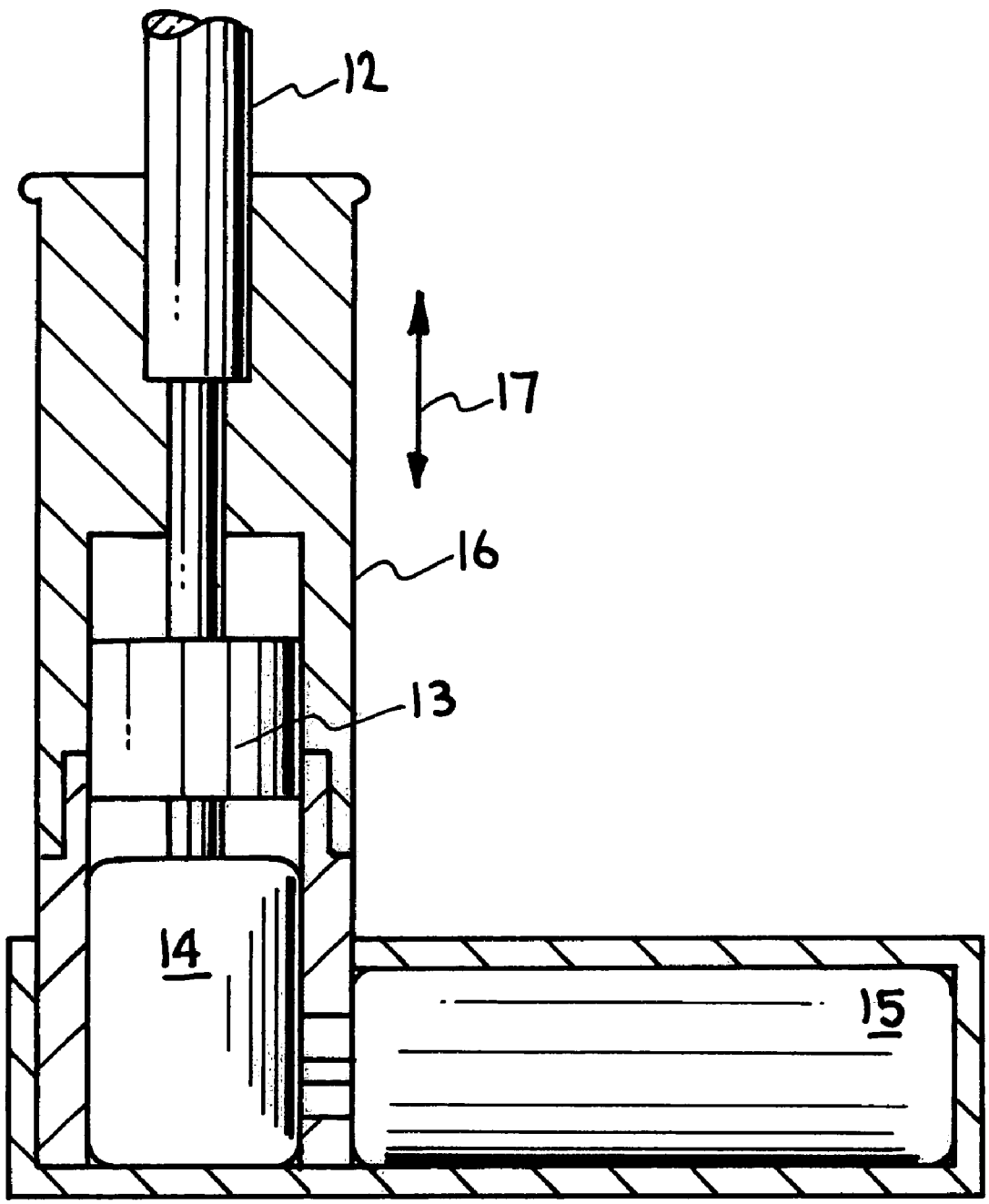
FIG. 2 shows additional details of the sample rotating turntable kit for an infrared spectrometer.

Referring now FIG. 2, additional details of the sample rotating turntable kit 10 for an infrared spectrometer are shown. The kit 10 includes a rotatable sample cup 13 containing the sample. The sample cup 13 is adapted to receive the probe 12. The probe is height adjustable and can be moved upward or downward as illustrated by the double headed arrow 17.

Infrared spectrometric analysis can be used to characterize non-homogeneous samples of unknown material. This requires that the sample be rotated slowly to "average" the exposed surface to the analyzing instrument. The rotator 14 rotates the sample cup 13. The rotator 14 includes an electric motor and a gear box. A battery 15 is connected to the electric motor in the rotator 14 and provides power to the electric motor for rotating the sample cup 13.

The probe 12 uses a fiber optic bundle to deliver and collect light.

Light exiting a fiber optic in the probe 12 reflects off of the sample and is partially absorbed at unique wavelengths based on the sample material. The reflected light is collected with a fiber optic in the probe 12 and dispersed onto a detector in the spectrometer 11 which measures the intensity of the reflected light compared to a reflectance standard.

A sleeve 16 is positioned proximate the sample cup 13 and is adapted to receive the probe 12. The sleeve 16 is an annular sleeve positioned above the sample cup 13 and adapted to receive the probe 12, keep the probe 12 aligned over the sample cup 13, and eliminate background light.

Figure 3:
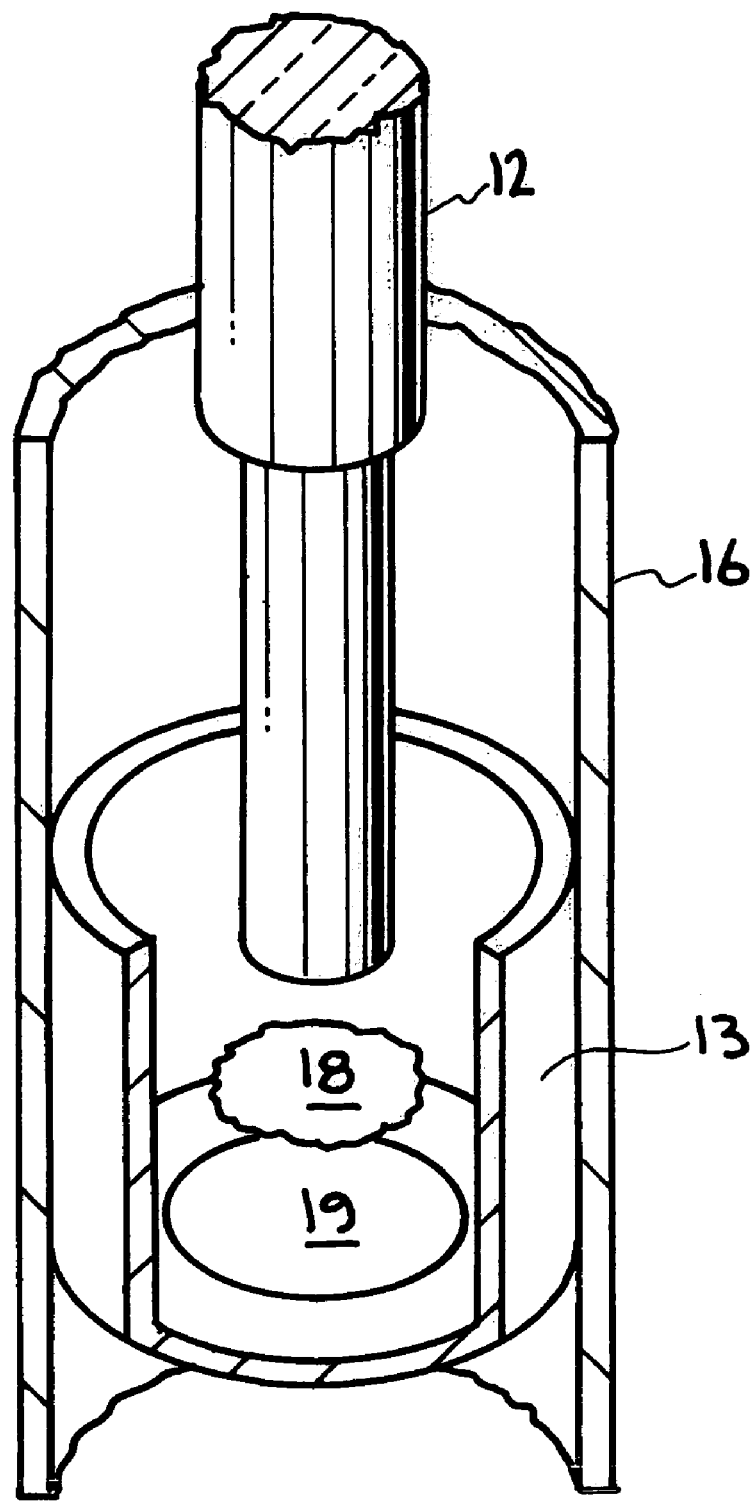
FIG. 3 shows an enlarged view of the sample cup.

Referring now FIG. 3, an enlarged view of the sample cup 13 is shown. The sample cup 13 receives the probe 12. The sample 18 to be analyzed is in the sample cup 13. The sleeve 16 is an annular sleeve positioned around the sample cup 13 and the probe 12. A reflectance standard 19 is located below the sample 18 in the rotatable sample cup 13.

For the NIR wavelength range, Spectrolon™ standards are available with 99% reflectance over the entire range of interest. For samples that do not cover the bottom of the cup 13, it is recommended to perform the analysis with the sample 18 on top of the reference material 19 to eliminate specular reflections from the bottom of the cup. The sample cup 13 can be coated with or made from diffusely reflective materials to normalize the background and eliminate the specular reflectance of the probe 12.

Light exiting a fiber optic in the probe 12 reflects off of the sample 18 and is partially absorbed at unique wavelengths based on the sample material. The reflected light is collected with a fiber optic in the probe 12 and dispersed onto a detector in the spectrometer which measures the intensity of the reflected light compared to the reflectance standard 19.

Referring now to FIGS. 1, 2, and 3 the operation of the sample rotating turntable kit 10 for an infrared spectrometer will be described. The kit 10 is a portable sample rotating turntable that can be used for spectroscopic analysis of small quantities of samples. The kit 10 is designed to be used with fiber optic bundles that are coupled to a light source and detector for reflectance measurements. The sample is placed in the sample cup 13 and the fiber optic bundle in the probe 12 is adjusted and set different heights above the bottom of the sample cup 13. This is important for bundles that vary in size or collection spot size. The fiber optic bundle is locked in place in the sleeve 16 that fits over the sample cup 13 to eliminate background light and keep the bundle aligned over the center of the sample cup 13. A reference 19 in the sample cup 13 contains a reflectance standard at the bottom of the cup which has a known reflectance over the wavelength of interest.

A prototype of the sample rotating turntable kit 10 was built. A test of the sample rotating turntable kit 10 for an infrared spectrometer was conducted. The spectrometer acquired full spectral scans at the rate of 10 samples per second and therefore the turntable was designed to rotate at a rate of 20 rpm. Samples of less than 10 mg were analyzed and their spectra compared favorably with those obtained from larger samples.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A sample rotating turntable kit for an infrared spectrometer having a probe for analyzing a sample, comprising:
    a rotatable sample cup containing the sample and adapted to receive the probe,
    a reflectance standard in said sample cup,
    a rotator for rotating said rotatable sample cup, and
    a battery connected to said rotator.

2. The sample rotating turntable kit for an infrared spectrometer of claim 1 wherein said rotatable sample cup of has a volume of 1 cm$^3$ or less.

3. The sample rotating turntable kit for an infrared spectrometer of claim 1 wherein said reflectance standard is located below the sample in said rotatable sample cup.

4. The sample rotating turntable kit for an infrared spectrometer of claim 1 wherein said reflectance standard is located above the sample in said rotatable sample cup.

5. The sample rotating turntable kit for an infrared spectrometer of claim 1 including a sleeve positioned proximate said sample cup and adapted to receive the probe.

6. The sample rotating turntable kit for an infrared spectrometer of claim 5 wherein the probe comprises a fiber optic bundle that encounters background light and wherein said sleeve is an annular sleeve positioned above said sample cup and adapted to receive the probe, keep the probe aligned over said sample cup, and eliminate said background light.

7. The sample rotating turntable kit for an infrared spectrometer of claim 1 including a diffusely reflective material coating said rotatable sample cup.

8. A portable infrared spectrometer sample rotating turntable apparatus, wherein the infrared spectrometer has a probe for analyzing a sample, comprising:
   a rotatable sample cup containing the sample and adapted to receive the infrared spectrometer probe,
   a reflectance standard in said sample cup,
   a sleeve positioned proximate said sample cup and adapted to receive the probe,
   a rotator for rotating said rotatable sample cup, and
   a battery connected to said rotator.

9. The portable infrared spectrometer sample rotating turntable apparatus of claim 8 wherein said rotatable sample cup of has a volume of 1 $cm^3$ or less.

10. The portable infrared spectrometer sample rotating turntable apparatus of claim 8 wherein said reflectance standard is located below the sample in said rotatable sample cup.

11. The portable infrared spectrometer sample rotating turntable apparatus of claim 8 wherein said reflectance standard is located above the sample in said rotatable sample cup.

12. The portable infrared spectrometer sample rotating turntable apparatus of claim 8 wherein the probe comprises a fiber optic bundle that encounters background light and wherein said sleeve is an annular sleeve positioned above said sample cup and adapted to receive the probe, keep the probe aligned over said sample cup, and eliminate said background light.

13. The portable infrared spectrometer sample rotating turntable apparatus of claim 8 including a diffusely reflective material coating said rotatable sample cup.

* * * * *